(12) United States Patent
Beaty

(10) Patent No.: US 6,223,749 B1
(45) Date of Patent: May 1, 2001

(54) CERVICAL BOARD AND METHOD OF USE

(76) Inventor: W Roger Beaty, P.O. Box 185, County Rd. 73, #149C, Tesuque, NM (US) 87574

( * ) Notice: Subject to any disclaimer, the term of this patent is extended or adjusted under 35 U.S.C. 154(b) by 0 days.

(21) Appl. No.: 09/460,950

(22) Filed: Dec. 14, 1999

Related U.S. Application Data

(60) Provisional application No. 60/112,407, filed on Dec. 15, 1998.

(51) Int. Cl.$^7$ .................................................. A61B 19/00
(52) U.S. Cl. .................. 128/869; 128/870; 128/DIG. 23; 5/630
(58) Field of Search ..................................... 128/845, 846, 128/869, 870, 876, DIG. 23; 5/630, 636; 602/18, 19

(56) References Cited

U.S. PATENT DOCUMENTS

| 3,278,230 | * | 10/1966 | Boyce | 128/820 |
| 4,141,368 | | 2/1979 | Meyer | 128/87 |
| 4,143,654 | | 3/1979 | Sherman | 128/87 |
| 4,299,211 | * | 11/1981 | Doynow | 128/870 |
| 4,515,153 | | 5/1985 | Calabrese | 128/75 |
| 4,732,144 | | 3/1988 | Cunanan | 128/878 |
| 4,739,752 | * | 4/1988 | Cohen | 128/882 |
| 4,886,052 | | 12/1989 | Calabrese | 128/75 |
| 5,205,813 | | 4/1993 | Schmidt | 602/17 |
| 5,515,869 | * | 5/1996 | Powell | 128/870 |
| 5,546,601 | | 8/1996 | Abeyta | 2/2 |
| 5,575,763 | | 11/1996 | Nagata et al. | 602/18 |
| 5,624,387 | | 4/1997 | McGuinness | 602/18 |
| 5,657,766 | | 8/1997 | Durham | 128/870 |
| 5,724,992 | * | 3/1998 | Ip | 128/870 |
| 5,795,315 | | 8/1998 | Traut et al. | 602/18 |

* cited by examiner

Primary Examiner—Michael A. Brown
(74) Attorney, Agent, or Firm—Heslin & Rothenberg, P.C.

(57) ABSTRACT

A device for stabilizing the cervical spine includes a generally U-shaped upper structure for fitting about the back and opposing sides of a head of a user, a lower support structure connected to and extending downwardly from the upper structure, a pair of shoulder restraints connected to and extending from the lower support structure in a forward and downward arcuate direction to overlie the upper thoracic region on opposite sides of the spinal column of the user. The lower support structure having a length extending to a position which would underlie the scapulas of the user, and a width being generally the approximate width of a person's back. The shoulder restraints having an interior side which substantially conforms with the shape of the posterior midline portions of the shoulders and upper thoracic region of the user.

19 Claims, 3 Drawing Sheets

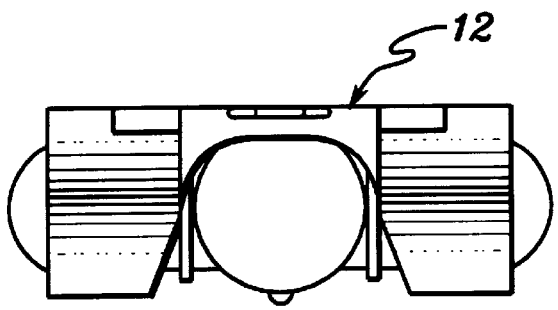
fig. 5
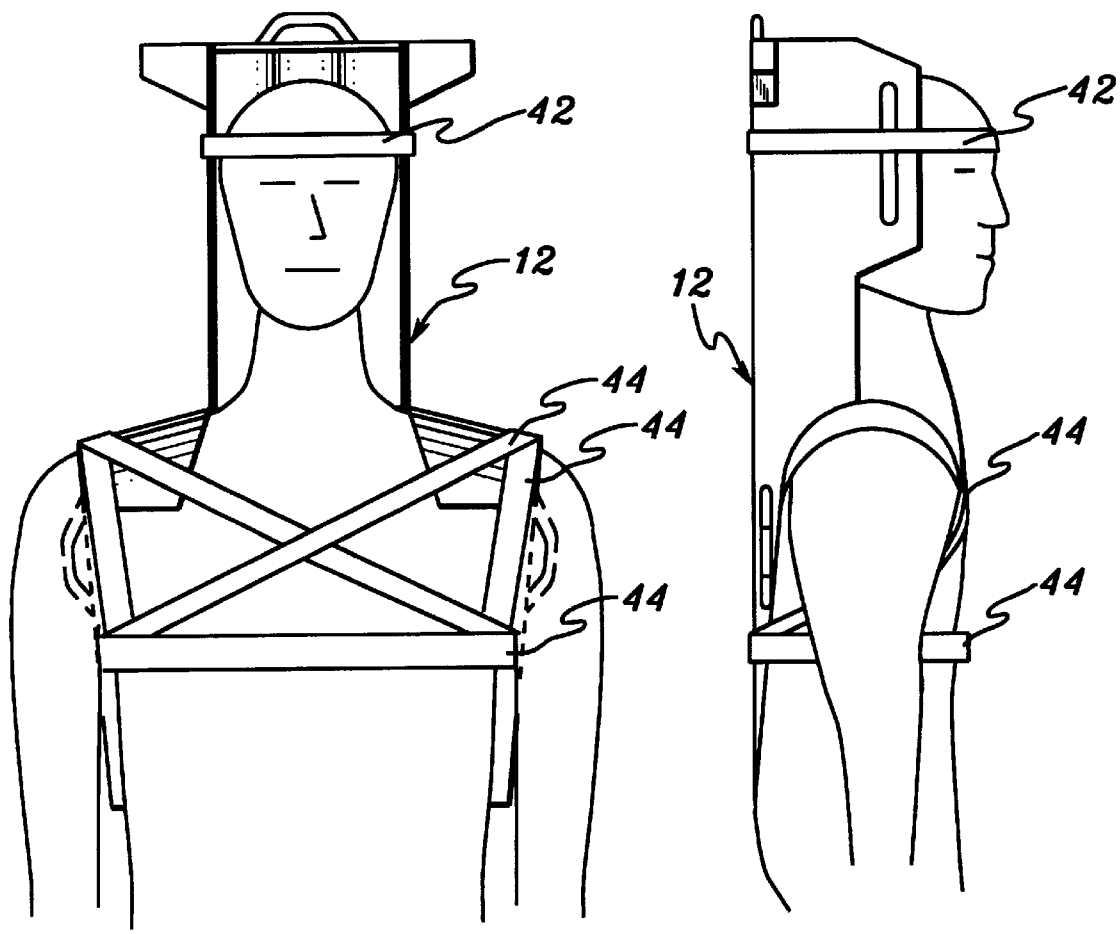
fig. 6
fig. 7

CERVICAL BOARD AND METHOD OF USE

This application claims priority of U.S. application Ser. No. 60/112,407, filed Dec. 15, 1998, the contents of which are hereby incorporated by reference.

BACKGROUND OF THE INVENTION

The present invention relates to a cervical board which is designed to provide motion restriction of a patient's cervical spine during an emergency medical or trauma situation.

Spinal trauma, if not recognized and properly managed in the field, can result in irreparable damage and potentially leave a patient paralyzed for life. Therefore, the initial treatment administered to a patient by emergency medical personnel can be critical to the future well-being of the patient. The cervical spine is comprised of the first seven vertebra of the spinal column, and is intended to bend, twist, and flex, all while supporting the head.

When it is suspected that a patient may have suffered injury to the cervical spine or neck region, or may be at risk for cervical spine injury during treatment, it is critical that emergency medical personnel immobilize the patient's head during treatment and transport to prevent the exacerbation or occurrence of such injury. The consequences of moving a patient with a missed spinal injury, or allowing him to move, can be devastating. Failure to properly immobilize a fractured spine, can result in a life threatening or life impairing injury.

Therefore any patient who has sustained an injury indicative of cervical spinal loading or stretching, significant injury above the clavicles, significant blunt trauma to the torso, head injury resulting in an altered level of consciousness, or a major fall should be presumed to have a cervical spine injury. Any such patient should be immobilized in a neutral in-line position before he is even slightly moved. Many of the emergency medical devices found in the prior art, however do not sufficiently restrict movement of the head and cervical spine and thus require supplemental means for achieving adequate mobilization.

Typically, the patient is fitted with a cervical collar by an emergency medical technician, while another emergency medical technician stabilizes the patient's head manually. When a patient is wearing a cervical collar, he does not have a stabilized or immobilize neck. True spinal immobilization occurs only when the patient is placed on a back board with their shoulders and hips strapped or taped down and the head is both taped down and stabilized laterally. Lateral stabilization presently occurs by wedging a pair of tapered blocks on either side of the head to prohibit lateral movement. Only after true spinal immobilization occurs may the emergency medical technician release his manual stabilization.

While a patient, wearing a cervical collar and secured to a backboard, is considered to be immobilized, a system of this type has inherent weaknesses. The patient's body is typically secured to the backboard by straps, while the head is taped to the backboard. Strapping a patient to a backboard does not immobilize their body; the slick surface of many backboards, allows for some body movement or sliding. Movement of the body while the head is in a fixed position compromises the cervical spine.

Also, the size and shape of a back board prohibit its use as an initial means of stabilization within a vehicle or other situations where space is at a premium. Therefore when extracting a patient from a vehicle, a cervical collar and manual stabilization are often the standard of care given a patient. A patient goes through a wide range of motions as they are extracted from a vehicle or confined space. A cervical collar by itself does not provide adequate cervical spine protection. The head can still move laterally, longitudinally and/or rotate. And as stated previously the slightest movement of the head and relation to the neck and cervical spine can cause irreparable damage. Once the patient has been extracted from the vehicle, they can be placed on a back board and properly stabilized.

Once a patient is secured to a backboard, the cervical collar may become a hindrance. The cervical collar provides limited access to the patient's neck. This increases the difficulty of performing a tracheotomy, starting intravenous infusions in the external jugular veins or treating neck trauma. Additionally, the cervical collar uses the patient lower jaw as an anchor point, thereby restricting movement. This inhibits communication between the emergency medical personnel and the patient, limits oral access, and creates a life threatening situation if the patient aspirates vomit.

Other devices, while also providing adequate immobilization of the head and cervical spine once the patient has been moved to a open work area, do not provide adequate access to the patients ears to permit emergency medical personnel to perform a complete diagnosis of the patient's condition. If it is believed that injury has occurred to the head or neck region, it is desirable that emergency medical personnel have access to the patients ears to observe fluid discharge from the ear. Also, along with limiting visibility of the ear, the patients hearing is obstructed.

A further weakness of the cervical collar surfaces once the patient arrives at the hospital. If there is strong suspicion that the patient may have a cervical spine injury he will remain on the backboard with the head restraint device in place. This occurs because the backboard and head restraint device are providing, in conjunction with one another, cervical spine motion restriction. The patient may remain on the backboard for hours while their cervical spine injury is assessed, which raises the concern of localized pressure injury to the patient. A patient on a backboard is typically in an unnatural position lying flat on his back, restrained from head to toe, on a hard, un-padded surface, with his head on the same plane as his shoulders. He cannot move or adjust position as he would if he were not restrained. When kept in this position for any length of time he will experience localized pressure, restricted blood flow and discomfort at any point that his body is in contact with the backboard. Restraining the patient's head on the same plane as his shoulders may cause hypo-flexion or hyper-extension of the cervical spine. It is desirable to get the patient of the backboard as soon as possible in order to avoid localized pressure and cervical spine hypo-flexion or hyper-extension complications.

Accordingly, there is a need for a head and neck immobilizer which can secure a patient's head and neck in a manner that prevents rotational, flexion and/or extension motion, while providing access to the patients neck, mouth and ears. This device should also be simple, quick and easy to apply to a patient in an emergency situation.

SUMMARY OF THE INVENTION

The invention, as claimed, is intended to provide a remedy. It provides cervical spine immobilization by securing a patient's head and neck in a manner which prevents rotational, flexion and/or extension motion while also providing access to the patient's neck, mouth and ears. The present invention allows a user to quickly and conveniently place and secure a cervical board to a patient with a suspected neck injury and thereby immobilize the patient's cervical spine.

The inventive cervical board is of a one piece design and comprises a head support with acruate side walls which prevents lateral movement of the patient's head, a support member which extends downwardly from the lower most portion of the head support and flanges out to form a back support which has a pair of shoulder restraints on opposite sides of the center line of the device.

The back support is approximately the width of a patient's back at its upper most portion and then tapers down in a manner which conforms with the shape of a person's torso. The support member and upper portion of the back support should be of sufficient strength and rigidity to resist any torque or twisting moments placed upon the device by lifting or other movement by the patient. When in use the lower edge of the back support should rest below the scapulas of the patient.

The shoulder restraints extend forward and downward substantially conforming to the shoulder and upper chest area of the patient. Once placed and secured, by medical tape or straps, within the inventive cervical board the shoulder restraints and back support coupled with the head support prevent any cervical movement by the patient.

The inventive design of the cervical board provides improved immobilization of the patient's cervical spine, while still allowing access to the patient's upper chest, neck, mouth and lower jaw. Because the patient is secured by the anterior and posterior portions of their shoulders and their head, the entire area from the upper chest to the upper jaw is exposed. This allows emergency medical personnel to treat external injuries to this area, insert airway adjunct devices, and start intravenous infusions in the external jugular veins while cervical spine immobilization is being maintained.

Also, the inventive design of the cervical board allows emergency medical personnel to fit a patient with the device while they are still in a vehicle or other area restrictive environment. This allows immediate stabilization of a patient's cervical spine thereby minimizing any undue movement or stress which may be caused by traditional methods.

The inventive cervical board also takes the anatomy of the cervical spine into consideration. In adults, the head support on the cervical board places the patient's head above the posterior plane of the shoulder blades to avoid hyperextension. In children, the pediatric version of the cervical board will place the patient's shoulders in a position higher than the posterior plane of the head support to avoid hyperflexion. Also the concave cross-section of the head support may be fitted with padding for comfort as well as providing lateral immobilization of the patient's head.

BRIEF DESCRIPTION OF THE DRAWINGS

One way of carrying out the invention is described in detail below with reference to the drawings which illustrate one or more specific embodiments of the invention and in which:

FIG. 5 is a top view of the present invention being used on a patient;

FIG. 6 is a front view of the inventive cervical board according to the present invention being used on a patient; and FIG. 7 is a side elevational view of the present invention being used on a patient.

DESCRIPTION OF THE PREFERRED EMBODIMENTS

Figure 1:
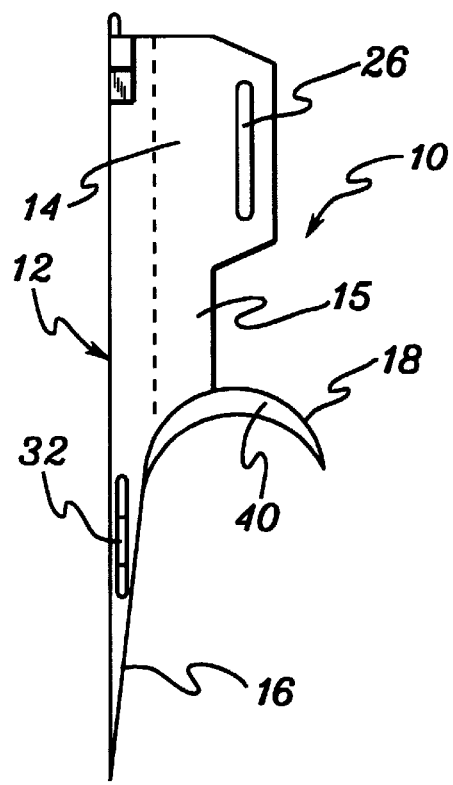
FIG. 1 is a side elevational view of the inventive cervical board according to the present invention.
Figure 2:
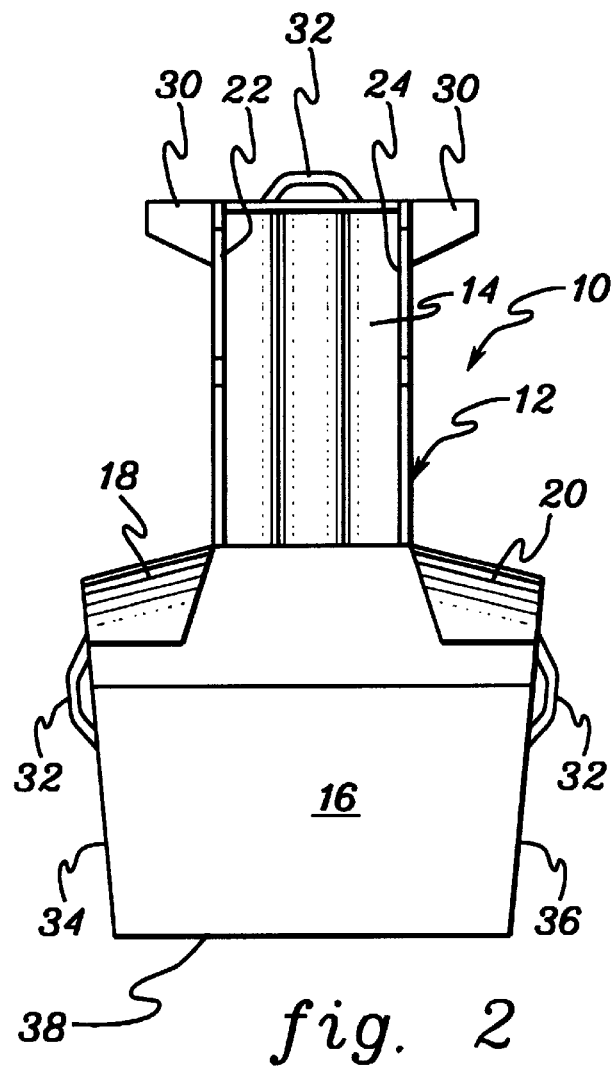
FIG. 2 is a top view of the inventive cervical board according to the present invention.
Figure 3:
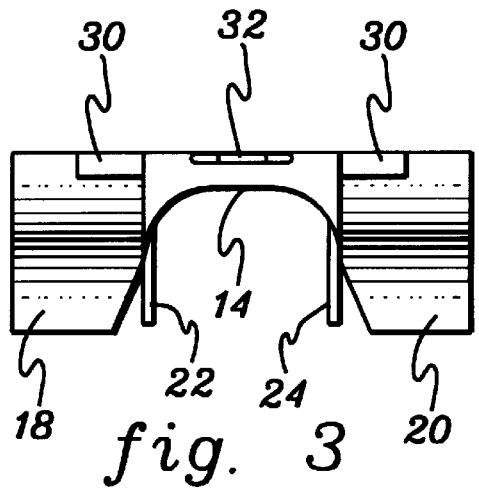
FIG. 3 is a front view of the inventive cervical board according to the present invention.

Referring to FIGS. 1–4, a preferred embodiment of the present invention is designated generally by the reference numeral 10. Cervical board 12 comprises a head support 14, neck 15, back support 16 and shoulder restraints 18 and 20. The inventive device is preferably constructed out of a thermoplastic material which will appear translucent when placed under an X-ray, such as plastic, polyolefin, polycarbonate, polystyrene, polypropylene, polytetrafluoroethylene, acrylonitrile butadiene-styrene or acrylic; however any suitable material may be used. The inventive device is preferably of a one-piece design, and is manufactured by injected plastic molding or other techniques known in the art. Alternatively the device may be constructed from a laminate of cardboard, paperboard or fiberglass or other such material as may be known in the art.

Head support 14 further comprises inner side walls 22 and 24. Inner side walls 22 and 24 are arcuate shaped and form substantially a half circle for fitting about the back and opposing sides of a patients head. Inner side walls 22 and 24 should be of sufficient height to restrain lateral movement of a patient's head and preferably extend to approximately the midline portion of a patients head.

The contact surfaces of cervical board 12 may be fitted with a dense foam padding, or other suitable padding material as may be known in the art, to aid with the comfort and provide surface friction for motion restriction and lateral stabilization of the patient's head. Such padding may be applied after manufacture of the cervical board by adhesive or other means known in the field.

Figure 4:
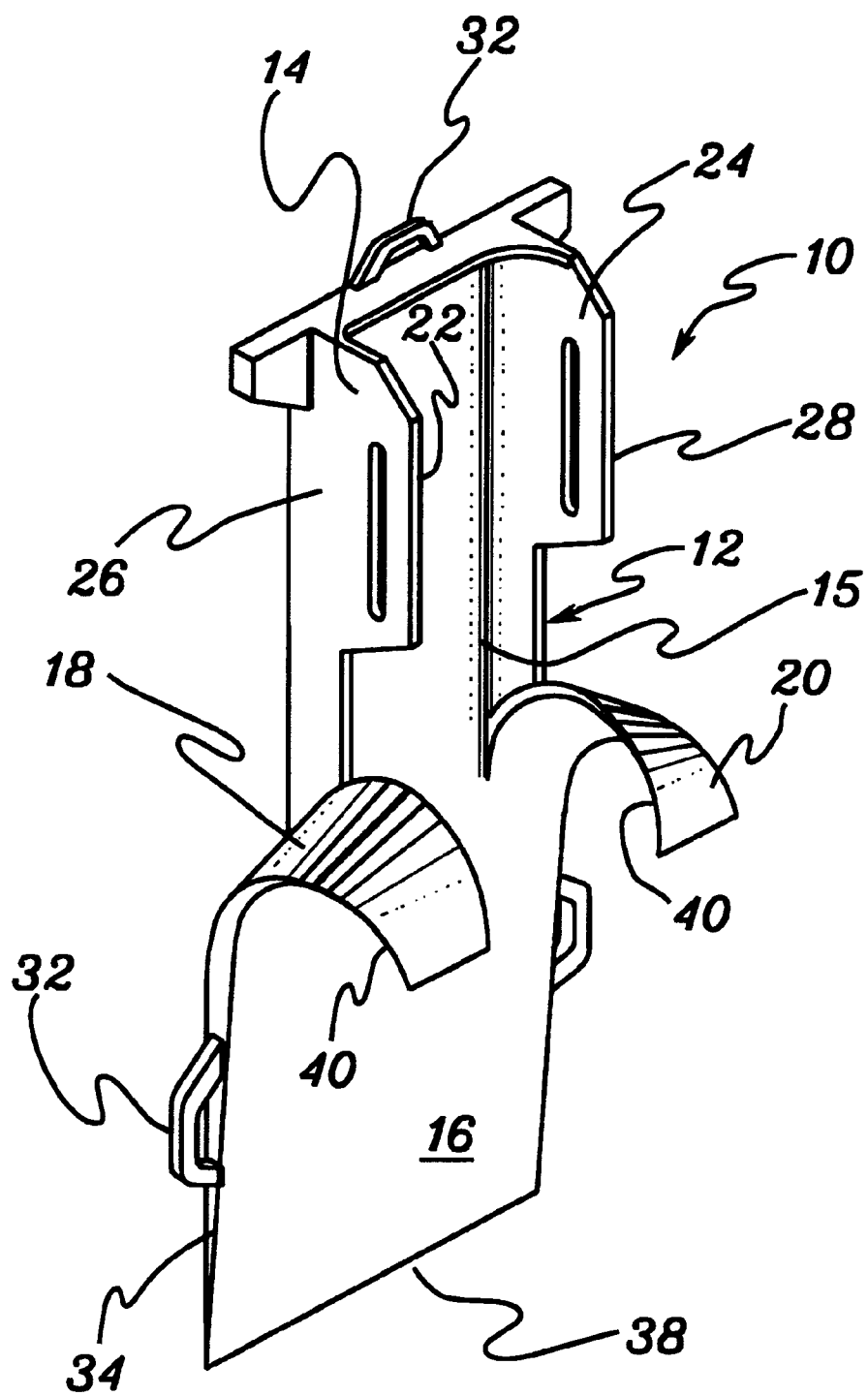
FIG. 4 is a perspective view of the inventive cervical board according to the present invention.

Defined within the inner and outer walls of head support 14 are a plurality of ear holes 26. Ear holes 26 should be of sufficient size and shape to allow visibility of the patients ears while also allowing communication between the emergency medical personnel and the patient. Ear holes 26 can be cut into head support 14 after its construction, or alternatively they may be part of the initial mold from which the device is constructed. Ear holes 26 may comprise a plurality of holes as shown in FIG. 4 or an elongated slot as shown in FIG. 1, or alternative configurations as may be known in the art.

A pair of flanges 30 are located at the upper most portion of head support 14. Flanges 30 extend outward from head support 14 a sufficient distance to allow emergency medical personnel to tape the cervical board to a large back board for transportation purposes.

A hand hold 32 is defined at the upper most portion of head support 14. Hand hold 32 is configured to allow an emergency medical technician a gripping recess to aid in lifting the cervical board once the patient is restrained, or as a carrying handle to carry the cervical board to the patient. Hand hold 32 should be of sufficient strength and durability to withstand the forces associated with lifting a patient from their initial treatment position to a supplemental position.

Neck 15 extends from the lower portion of head support 14 and terminates at the upper most portion of back support 16. Neck 15 is generally the same width as head support 14 and should be of sufficient strength and durability to withstand any torque or twisting forces which may accompany lifting a patient, or restricting a patients movement. The length of neck 15 should approximate the length of a persons neck. However, since people's necks vary in size from adolescence to large adults, the inventive device may also be produced in various sizes. Therefore the length of neck 15 may vary to accommodate a wide variety of patients.

Back support 16 has outer edges 34 and 36 and a lower edge 38. Back support 16 has a width at its upper most point which is approximately the width of the back of the user. Outer edges 34 and 36 begin at the upper most portion of back support 16 and taper inward to substantially conform to the shape of a person's upper torso. Outer edges 34 and 36 terminate at lower edge 38. When fitted on a patient lower edge 38 preferably underlies the scapulas of the patient. Therefore similar to varying the sizes of neck 15 to accommodate various sized patients, the length of outer edges 34 and 36, and the width of lower edge 38 can be varied.

The cross-sectional width of back support 16, is greatest at the upper most portion where back support 16 and neck 15 join. The cross-sectional width then diminishes uniformly until its termination at lower edge 38. The cross sectional width of the upper portion of back support 16 and neck 15 should be sufficient to prevent any torque of the cervical board when lifting or moving a patient. Also it may be desirable to place recessed handholds (not shown) in the back support portion of the cervical board.

Connected to and extending downwardly from the upper most portion of back support 16 are a pair of semi-rigid U-shaped shoulder restraints 18 and 20. Shoulder restraints 18 and 20 have an inside edge 40 which substantially conforms to the upper thoracic region on opposite sides of the spinal column of the user. Shoulder restraints 18 and 20 should have sufficient strength and rigidity to restrain the user. Shoulder restraints 18 and 20 may be serrated horizontally on their interior surface to allow for greater flexation which may be useful when applying the device in confined spaces or allowing for flat storage in a rescue vehicle or other storage area.

When it is desired to employ the present invention, the inventive cervical board can be slipped over a patient's shoulders from above and behind and in the manner of a strapless backpack, as illustrated in FIGS. 5–7., This can be done while the patient is in a vehicle or other area where space is limited. As seen from the front, the cervical board rests over the top of the patients shoulders and extends a few inches down the patients chest. As seen from the back, the cervical board rests over the patients shoulders and extends downward past the scapulas and upwards beyond the patients head.

Once the cervical board is placed over a patients shoulders, the patient would be secured to the cervical board, and the cervical spine becomes immobilized.

The patient is secured to the cervical board by placing a body restraint 44 under the patients arm and around the patients chest. Alternatively, body restraint 44 may be crossed over the patient's chest in a "X" fashion. Body restraint 44 can be a piece of medical tape or the cervical board may be fitted with a nylon strap or straps which have Velcro or similar type fasteners.

The patient is then further secured to the cervical board by placing a head restraint 42 across the patients forehead. Head restraint 42 can be a piece of medical tape or the cervical board may be fitted with a nylon strap which has a Velcro fastener.

Once the patient's upper torso and head have been secured to the cervical board, the patient's cervical spine has been immobilized. The patient is secured to the cervical board by a broad based triangle formed by the left shoulder/shoulder blade, right shoulder/shoulder blade, and the back and sides of the head. The cervical spine itself is not directly secured to the cervical board, instead the large body masses on each end of the cervical spine are secured. Securing the head and shoulders will automatically immobilize the patients cervical spine. When the patient lies supine on the cervical board the weight of his upper body across the shoulder blades will provide additional rigidity to the cervical board, aiding in the immobilization of the cervical spine.

When most adults are supine, the head tips backwards into a hyper-extended position, compromising both the patients airway and cervical spine. Upon arrival, emergency medical personnel generally move the head into a neutral in-line position and manually maintain it in the position, which in a typical adult requires holding the head off of the ground.

In typical adults, when the head is placed in a neutral in-line position, the outer measurement of the occipital region at the back of the head is between ½ inch and 3½ inches above the posterior plane of their back. Therefore, when laid on a flat surface, in a neutral in-line position, most adults have a space between the back of the head and the flat surface. However, when using the inventive cervical board, head support 14 should position a patient's head in the neutral in-line position. This is accomplished by the posterior plane of head support 14 being raised above the posterior plane of back support 16. By raising head support 14 the patient's head will remain in the neutral in-line position when the cervical board is applied.

In small children (generally those having a body size of a seven-year old or younger) the size of the head is much larger relative to the rest of the body then it is in adults, and the muscles of the back are less developed. When a small child's head is in a neutral and-line position, the back of the head usually extends between one inch and two inches below the posterior plane of their back. Therefore, when a small child is placed directly on a flat surface their head will be moved into a position of flexion, compromising their airway and cervical spine.

To compensate for the discrepancy between child and adult anatomy sizes, the cervical board can be manufactured specifically for children or infants. This is done by lowering the posterior plane of head support 14 to a position below the posterior plane of back support 16. By lowering head support 14 a child's head will remain in the neutral in-line position when the cervical collar is applied.

Alternatively, the inventive device may provide cervical spine motion restriction for people wearing helmets. A patient wearing a helmet creates several problems for emergency medical personnel; the patient cannot lie supine without compromising their airway and it is hard to stabilize the slick, hard, round shape of the helmet to a hard, flat surface.

A person wearing a helmet has a head to body proportion that is similar to a child. If placed supine on a flat surface their head will tilt forward in a chin-down position. This can cause hypoflexion of the cervical spine as well as compromising the airway. A cervical board which raises the shoulders above the level of the back of the helmet will help bring the cervical spine to a neutral, in-line position. Additionally, the padded interior curve of the head restraint of a cervical board will adapt to the curve of a helmet, thereby reducing any movement of the helmet in relation to the cervical board to provide stabilization of the patient's cervical spine.

While illustrative embodiments of the invention have been described above, it is, of course, understood that various modifications will be apparent to those of ordinary skill in the art. Many such modifications are contemplated as being within the spirit and scope of the invention.

What is claimed is:

1. A cervical spine stabilizing device, comprising:
   (a) an upper structure for fitting about the back and opposing sides of a head of a user;
   (b) a lower support structure connected to and extending downwardly from said upper structure, said lower support structure having a length, a width, and a thickness, said length extending to a position which would underlie the scapulas of the user, said width being generally the approximate width of a person's back, and said thickness tapering in a substantially uniform manner from a first thickness to a second thickness, wherein said first thickness is greater than said second thickness; and
   (c) a pair of shoulder restraints, said shoulder restraints connected to and extending from said lower support structure.

2. The device of claim 1 wherein said device comprises one piece.

3. The device of claim 1 wherein said upper structure is on a first plane, and said lower support structure is on a second plane.

4. The device as in claim 3 wherein said first plane is different from said second plane.

5. The device as in claim 1 further comprising a cushioning layer secured to said upper structure.

6. The device as in claim 5 wherein said cushioning layer comprises foam rubber.

7. The device as in claim 1 further comprising fastening means for releasably securing the user to said device.

8. The device as in claim 7 wherein said fastening means comprises adhesive tape.

9. The device as in claim 1 wherein said device comprises at least one of thermoplastic, cardboard, and fiberglass.

10. A cervical spine stabilizing device, comprising:
    (a) a generally U-shaped upper structure;
    (b) a lower support structure connected to and extending downwardly from said generally U-shaped upper structure, said lower support structure having a first thickness in a first portion sufficient to prevent torsional movement of said lower support structure in said first portion, and said lower support structure having a second thickness in a second portion, wherein the thickness of said lower support structure tapers in a substantially uniform manner from said first thickness to said second thickness, wherein said first thickness is greater than said second thickness; and
    (c) a pair of shoulder restraints, said shoulder restraints connected to and extending from said lower support structure.

11. The device of claim 10 wherein said device comprises one piece.

12. The device of claim 10 wherein said upper structure is on a first plane, and said lower support structure is on a second plane.

13. The device as in claim 12 wherein said first plane is different from said second plane.

14. The device as in claim 10 further comprising a cushioning layer secured to said upper structure.

15. The device as in claim 14 wherein said cushioning layer comprises foam rubber.

16. The device as in claim 10 further comprising fastening means for releasably securing the user to said device.

17. The device as in claim 16 wherein said fastening means comprises adhesive tape.

18. The device as in claim 10 wherein said device comprises at least one of thermoplastic, cardboard, and fiberglass.

19. A method of stabilizing the cervical spine, comprising: placing a device onto a user, said device comprising
    (a) an upper structure for fitting about the back and opposing sides of a head of a user;
    (b) a lower support structure connected to and extending downwardly from said upper structure, said lower support structure having a length, a width, and a thickness, said length extending to a position which would underlie the scapulas of the user, and said thickness tapering in a substantially uniform manner from a first thickness to a second thickness, wherein said first thickness is greater than said second thickness; and
    (c) a pair of shoulder restraints, said shoulder restraints connected to and extending from said lower support structure; and
   securing said device to the user such that the cervical spine of the user is stabilized.

* * * * *